(12) United States Patent
Liu et al.

(10) Patent No.: US 11,453,007 B2
(45) Date of Patent: *Sep. 27, 2022

(54) NON-INVASIVE PRENATAL TEST ON SINGLE FETAL CELLS ISOLATED FROM BLOOD OF PREGNANT WOMEN

(71) Applicant: Lian Liu, Tarzana, CA (US)

(72) Inventors: Lian Liu, Tarzana, CA (US); Shuang Hou, Westlake Village, CA (US); Chun-Hao Luo, Agoura Hills, CA (US)

(73) Assignee: Lian Liu, Tarzana, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/930,410

(22) Filed: May 12, 2020

(65) Prior Publication Data
US 2020/0269245 A1 Aug. 27, 2020

Related U.S. Application Data

(63) Continuation of application No. 16/224,576, filed on Dec. 18, 2018, now Pat. No. 11,192,110.

(51) Int. Cl.
B01L 3/00 (2006.01)
A61B 5/15 (2006.01)
C12N 5/09 (2010.01)
G01N 33/50 (2006.01)

(52) U.S. Cl.
CPC ...... *B01L 3/502761* (2013.01); *A61B 5/1405* (2013.01); *C12N 5/0693* (2013.01); *G01N 33/5094* (2013.01); *B01L 2200/0668* (2013.01); *B01L 2300/088* (2013.01); *B01L 2300/0822* (2013.01); *B01L 2300/0848* (2013.01);

(Continued)

(58) Field of Classification Search
CPC ....... B01L 3/502761; B01L 2300/0874; B01L 2300/12; B01L 2200/0668; B01L 2300/088; B01L 2300/0864; B01L 2300/0848; B01L 2300/0822; B01L 3/502707; G01N 33/5094; G01N 33/5436; C12N 5/0693; A61B 5/1405; C12M 25/06

See application file for complete search history.

(56) References Cited

U.S. PATENT DOCUMENTS 8,186,913 B2 5/2012 Toner et al.
8,304,230 B2 11/2012 Toner et al.
8,784,012 B2 7/2014 Toner et al.
(Continued)

FOREIGN PATENT DOCUMENTS

WO 2015153816 A2 10/2015

OTHER PUBLICATIONS

Li, et al., "Binding of Streptavidin to Surface-attached Biotin with Different Spacer Thicknesses," Journal of Wuhan University of Technology-Mater, Sci. Ed.., vol. 30, No. 6, Dec. 2015, 1304-1309.

(Continued)

*Primary Examiner* — Christopher L Chin

(57) ABSTRACT

Methods and systems are provided for isolating fetal cells from a maternal blood supply in order to perform non-invasive prenatal testing. In one example, a system for non-invasive prenatal testing includes a substrate coated with a cell-capturing surface, the cell-capturing surface including an array of pillar-like structures, each pillar-like structure including a plurality of intersecting arms.

9 Claims, 8 Drawing Sheets

(52) U.S. Cl.
CPC ............... *B01L 2300/0864* (2013.01); *B01L 2300/0874* (2013.01); *B01L 2300/12* (2013.01)

(56) References Cited

U.S. PATENT DOCUMENTS

| | | |
|---|---|---|
| 9,034,658 B2 | 5/2015 | Barber et al. |
| 10,688,492 B2 * | 6/2020 | Liu .................... G01N 33/5094 |
| 10,786,813 B2 | 9/2020 | Liu |
| 2003/0148401 A1 | 8/2003 | Agrawal et al. |
| 2005/0273995 A1 | 12/2005 | Kanagasabapathi et al. |
| 2009/0018033 A1 | 1/2009 | Morgan et al. |
| 2011/0160869 A1 | 6/2011 | Duch et al. |
| 2013/0330246 A1 | 12/2013 | Stemmet |
| 2014/0315213 A1 | 10/2014 | Nagrath et al. |
| 2015/0368599 A1 | 12/2015 | Maher et al. |
| 2016/0123857 A1 | 5/2016 | Kapur et al. |
| 2016/0202123 A1 | 7/2016 | Jung et al. |
| 2016/0214107 A1 | 7/2016 | Viasnoff et al. |
| 2017/0038285 A1 | 2/2017 | Zheng et al. |
| 2018/0066299 A1 | 3/2018 | Kim et al. |
| 2019/0097257 A1 | 3/2019 | Dutta |

OTHER PUBLICATIONS

Walper, et al., "Comparison of single domain antibody immobilization strategies evaluated by surface plasmon resonance," Journal of Immunological Methods, 388 (2013), pp. 68-77.

* cited by examiner

NON-INVASIVE PRENATAL TEST ON SINGLE FETAL CELLS ISOLATED FROM BLOOD OF PREGNANT WOMEN

CROSS REFERENCE TO RELATED APPLICATIONS

The present application claims priority to 1) U.S. Provisional Patent Application Ser. No. 62/594,941, entitled "A Method and Device for CTC Capture and Characterization", filed on Jul. 6, 2018, 2) U.S. Provisional Patent Application Ser. No. 62/694,944, entitled "Non-Invasive Prenatal Test on Single Fetal Cells Isolated from Blood of Pregnant Women", filed on Jul. 6, 2018, 3) U.S. Provisional Patent Application Ser. No. 62/694,945, entitled "Simple and Eco-Friendly Fabrication of Biocompatible Micropillar Array Substrate (MAS) Using Micro-Imprinting", filed on Jul. 6, 2018. The entire contents of the above-identified applications are incorporated herein by reference for all purposes.

This application has subject matter in common with: 1) U.S. Nonprovisional patent application Ser. No. 16/282,583 entitled "Methods and Systems for Circulating Tumor Cell Capture" and filed on Feb. 22, 2019, and 2) U.S. Nonprovisional patent application Ser. No. 16/282,640 entitled "Biocompatible Micropillar Array Substrate and Methods for Fabricating Such Substrate and filed on Feb. 22, 2019, the entire disclosures of which are incorporated herein by reference.

FIELD

The present description relates generally to non-invasive prenatal tests, and more specifically to isolating single fetal cells from a maternal blood sample for cell-based non-invasive prenatal testing.

BACKGROUND

Standard methods for prenatal testing include invasive techniques such as amniocentesis, which may pose a risk to the developing fetus. As average parental age has advanced, the availability of accurate genetic testing has improved, and gene therapy technology has been developed, the push for accurate, early, and non-invasive prenatal testing techniques has increased.

SUMMARY

In one embodiment, a system for non-invasive prenatal testing includes a substrate coated with a cell-capturing surface, the cell-capturing surface including an array of pillar-like structures, each pillar-like structure including a plurality of intersecting arms.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
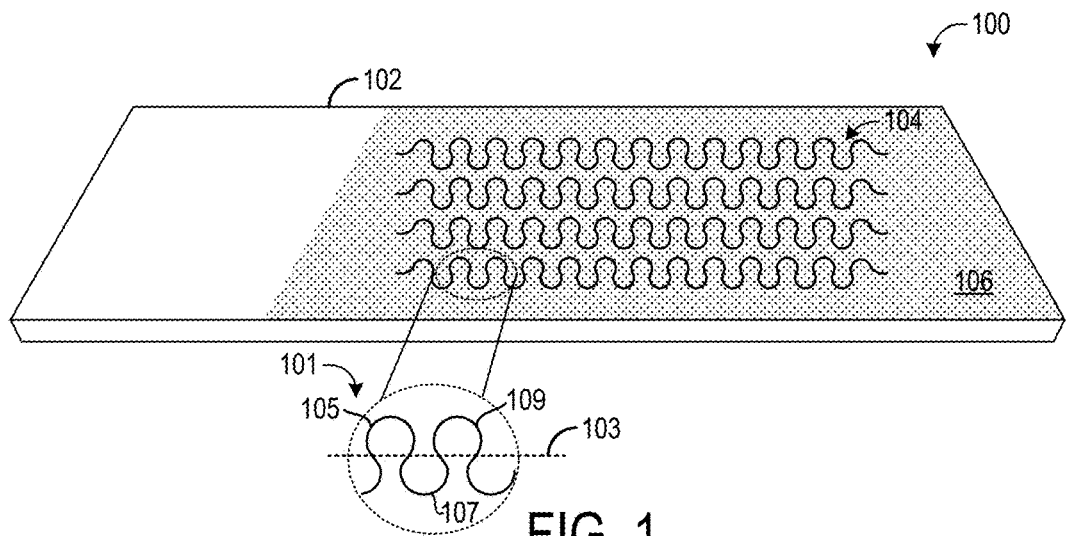
FIG. 1 schematically illustrates an example polymer-coated laser microdissectible (PCLMD) chip.

The following description relates to systems and methods for cell-based non-invasive prenatal testing. Non-invasive prenatal testing (NIPT) offers a new optional method of prenatal testing without harming the fetus and benefiting pregnant women who are at risk for miscarriage. The major factors driving the growth of this research field and technique development include the growing interest for non-invasive techniques over invasive methods, the safety and convenience promised by NIPT, and increasing maternal age (associated with growth in the risk of chromosomal abnormalities in babies). Furthermore, with the development of gene therapy technology, such as gene editing technology, early detection and treatment rely more on simple and accurate pre-delivery diagnostics.

Other NIPT techniques include cell-free DNA-based NIPT (cfDNA-based NIPT), in which fetal DNA circulating in maternal blood is isolated and then subject to desired genetic analysis. While such an approach offers a low-risk mechanism by which to test fetal DNA, the accuracy of cfDNA-based NIPT relies on the proportion of extracted DNA that is derived from the fetus, which may vary from patient to patient. Further, cfDNA-based NIPT relies on statistical methods that, while powerful, are not a sufficient substitute for direct biological measurements. Owing to the lack of intact genomic information, it may be difficult or impossible to detect all types of genetic disorders, such as single gene disorders, when relying on cfDNA-based NIPT.

Cell-based NIPT testing technologies are more accurate, as cell-based techniques supply whole genome sequencing information, providing more reliable results with satisfactory integrity of genomic DNA and potential for review of emerging new genomic markers of genetic diseases. However, cell-based NIPT still presents several challenges in developing accurate and robust NIPT, such as the need for a highly specific and efficient method for sorting target cells, the need for a reliable and simple method for target cell identification, and the need for a whole genome amplification method with high coverage and confidence on single cell level. For example, fetal cells circulating in maternal blood are relatively rare, and protocols to enrich the proportion of the fetal cells isolated from the maternal blood may result in loss or damage of the fetal cells. Further, it may be difficult to identify a fetal cell and differentiate the fetal cell from circulating maternal cells, in a gender-independent manner.

Thus, according to embodiments disclosed herein, cell-based NIPT may be carried out by isolating target fetal cells from a maternal blood sample by flowing the maternal blood sample through a polymer-coated laser micro-dissectible (PCLMD) chip. The PCLMD chip may be configured to immobilize certain fetal cells, such as trophoblast cells, and as such may be configured to selectively trap the fetal trophoblast cells while allowing maternal cells to flow through the chip. The PCLMD chip may include a bottom slide having a polystyrene (or other polymer) coated surface that includes a plurality of cell-capturing structures. The cell-capturing structures may include a plurality of pillar-like structures imprinted on the polystyrene membrane to form an array. The pillar-like structures may have a shape that is adapted to preferentially trap target fetal cells while allowing maternal cells to flow over the polystyrene surface and out of the PCLMD chip. For example, the pillar-like structures may include multiple, intersecting arms (e.g., four or eight arms arranged in a cross or double-cross structure), may have a height of 0.5 µm, and may have an overall diameter of 10 µm, which may assist in trapping fetal trophoblast cells, which are relatively large (e.g., 16 µm in diameter) compared to maternal blood cells (e.g., white blood cells may have a diameter of 6 µm).

The PCLMD chip may further include a corresponding top piece that, when placed on the bottom slide, forms one or more microfluidic channels. The microfluidic channels may be curved in a switch-back manner, which may cause the target fetal cells, which are larger than the maternal blood cells, to be retained in the microfluidic channels for a longer time than the smaller maternal cells. Together, the curved microfluidic channels and pillar-like structures imprinted on the surface of the bottom slide (and hence on the surface of the microfluidic channels) preferentially immobilize the target fetal cells. To further enhance the isolation of target fetal cells within a maternal blood sample, the PCLMD chip may be functionalized with antibodies specifically targeting the fetal cells of interest. For example, using biotin and neutravidin as linkers, antibodies specific to trophoblast cells may be coupled to the polymer surface of the bottom slide of the PCLMD chip.

After the prepared maternal blood sample has been flowed through the PCLMD chip, any immobilized fetal cells may be identified and differentiated from maternal cells using immunostaining and/or based on the size of the immobilized cell. Once an immobilized fetal cell has been identified, the fetal cell may be captured via laser dissection and whole genome amplification may be performed on the captured fetal cell. In this way, intact, genomic DNA may be obtained from a fetal cell, where the fetal DNA is usable for suitable genetic testing.

Turning now to FIG. 1, a polymer-coated laser microdissectible (PCLMD) chip 100 is shown. PCLMD chip 100 includes a substrate 102, such as a glass slide, having a top surface. A set of curved microfluidic channels 104 are printed (e.g., etched) on the top surface of the substrate. The set of curved microfluidic channels may include a first curved microfluidic channel, a second curved microfluidic channel, and so forth. As shown, the set of curved microfluidic channels 104 includes four separate curved microfluidic channels. Each curved microfluidic channel has a curved, switch-back pattern. As shown in more detail in the magnified portion 101, the curved switch-back pattern includes a repeating pattern of a top curved portion fluidly coupled to a bottom curved portion, where the top curved portion and bottom curved portion are reversed relative to each other across a longitudinal axis 103. For example, a first top curved portion 105 extends from a first point on the longitudinal axis to a second point on the longitudinal axis in a shape that constitutes approximately 75% of a circumference of a circle. Likewise, a first bottom curved portion 107 extends from the second point on the longitudinal axis to a third point on the longitudinal axis in a shape that constitutes approximately 75% of a circumference of a circle. A second top curved portion 109 extends from the third point on the longitudinal axis to a fourth point on the longitudinal axis in a shape that constitutes approximately 75% of a circumference of a circle, and so forth. The circular shape of each curved portion may have a diameter of 1.0 mm (outer diameter)/0.64 mm (inner diameter), although other dimensions are possible, such as an outer diameter of 0.9-1.1 mm and an inner diameter of 0.6-0.7 mm.

The top surface of substrate 102 is at least partially coated in a polymer membrane 106. The coating of the substrate with the membrane is performed such that the top/outer surfaces of the set of curved microfluidic channels 104 are also coated in the polymer membrane 106. The polymer membrane 106 may be comprised of a suitable polymer, such as such as a polystyrene-amine, and may have a suitable thickness, such as 2-5 µm. As will be explained in more detail below with respect to FIGS. 3 and 4, the polymer membrane 106 may be imprinted with a macro structure array configured to selectively immobilize fetal cells. Further, as explained in more detail below with respect to FIGS. 5 and 6, the polymer membrane 106 may be functionalized with specific antibodies that are configured to bind to a surface of target fetal cells.

Figure 2:
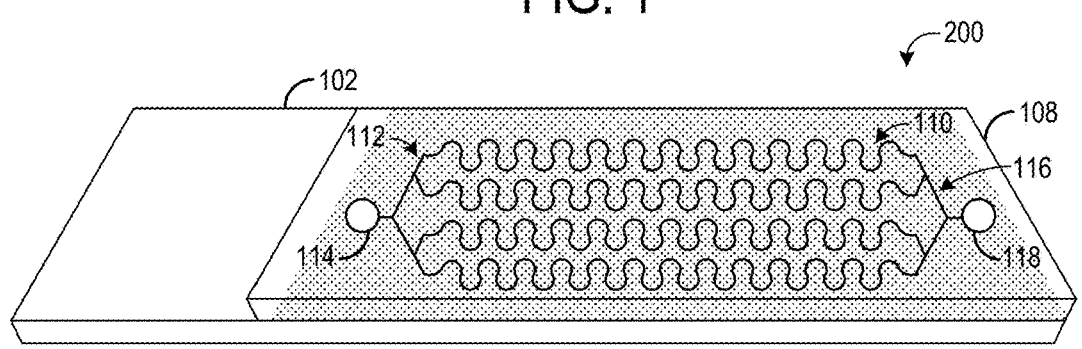
FIG. 2 schematically illustrates an example PCLMD chip system.

FIG. 2 shows a schematic diagram of a PCLMD chip system 200. PCLMD chip system 200 includes the substrate 102 described above with respect to FIG. 1, where the substrate 102 has a set of microfluidic channels imprinted on the surface and the surface is coated with a polymer membrane having a macro structure array. PCLMD chip system 200 further includes a top piece 108. The top piece 108 may be comprised of a silicone polymer such as polydimethylsiloxane (PDMS) or other suitable polymeric material. The top piece 108 may include a corresponding set of microfluidic channels printed on a bottom surface of the top piece 108 (e.g., a surface facing a top surface of the substrate 102). Thus, when the top piece 108 is positioned on top of substrate 102 as shown in FIG. 2, the bottom surface of the top piece 108 is in face-sharing contact with the top surface (and/or polymer membrane) of the substrate and a set of enclosed microfluidic channels 110 is formed. The enclosed microfluidic channels 110 may be comprised of the microfluidic channels 104 printed on the top surface of the substrate 102 and the microfluidic channels printed on the bottom surface of the top piece 108. The microfluidic channels printed on the bottom surface of the top piece 108 may be identical in size and shape to the microfluidic channels 104 printed on the top surface of the substrate 102. In this way, substrate 102 may include at least one first curved microfluidic channel and top piece 108 may include at least one second curved microfluidic channel. When the top piece 108 is positioned on substrate 102, a respective first curved microfluidic channel may align with a respective second curved microfluidic channel to form an enclosed curved microfluidic channel. In other examples, only substrate 102 may include the curved microfluidic channels. For example, the microfluidic channels may only be formed on the substrate 102 and the top piece 108 may be substantially flat. In either case, the enclosed microfluidic channels may have an overall depth of 70 µm and an overall width of 0.36 mm, although other dimensions are possible, such as a depth of 60-80 µm and a width of 0.3-0.4 mm. By providing microfluidic channels having the above dimensions, the flow rate through the channels and/or residence time of the cells through the channels may be such that the target fetal cells are preferentially isolated in the channels while the maternal cells flow through and out of the channels.

Top piece 108 further includes an inlet 114 coupled to an inlet manifold 112 and an outlet 118 coupled to an outlet manifold 116. The inlet manifold 112 may couple the inlet 114 with the enclosed microfluidic channels 110 (on a first side of the enclosed microfluidic channels) and the outlet manifold 116 may couple the outlet 118 with the enclosed microfluidic channels 110 (on a second side of the enclosed microfluidic channels). In this way, fluid may be supplied to the enclosed microfluidic channels 110 via inlet 114 and inlet manifold 112, and fluid may flow through each of the enclosed microfluidic channels. Fluid that is supplied to inlet 114 may be supplied by a suitable pump, such as a syringe pump, or other fluid supply mechanism. After flowing through the enclosed microfluidic channels, the fluid may be directed to the outlet 118 via the outlet manifold 116. Unlike the bottom portion, the top piece 108 may not be coated in a separate polymer membrane and may not include imprinted macro structures or linked antibodies. In this way, when the fluid (e.g., the maternal blood sample) flows through the enclosed microfluidic channels of the PCLMD chip system, the target fetal cells may be immobilized on the polymer membrane on the top surface of the substrate. The top piece 108 may then be removed to facilitate laser dissection of the membrane of the bottom portion in the region of an immobilized fetal cell.

Figure 3:
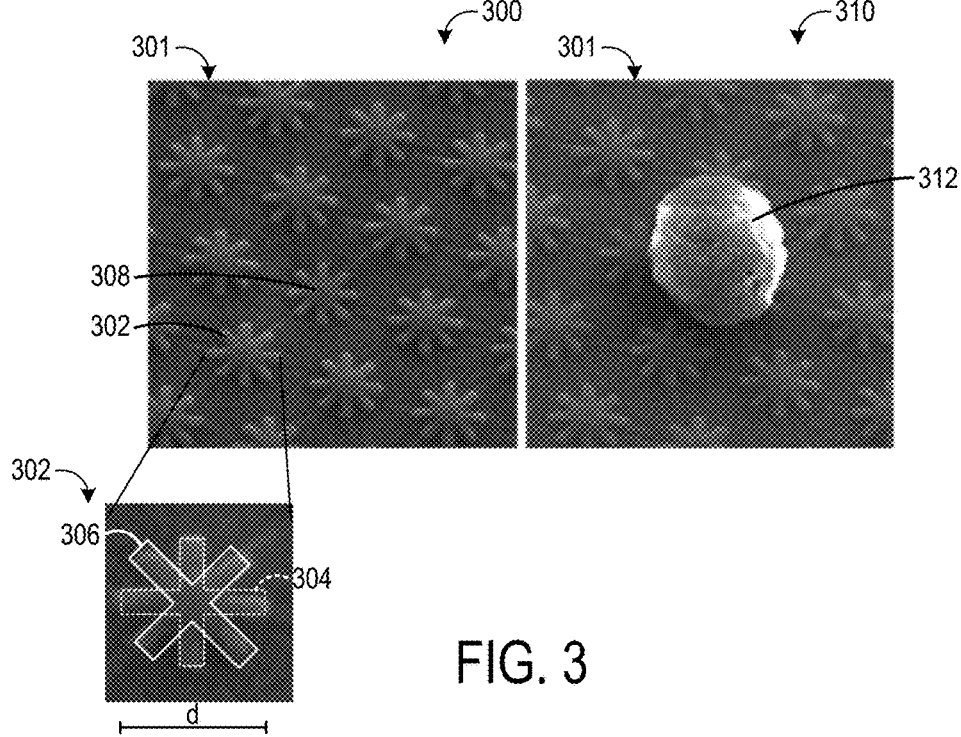
FIG. 3 shows two example images of a macro structure array imprinted on a polymer membrane of a PCLMD chip.

FIG. 3 shows a first image 300 of a macro structure array 301 imprinted on a polymer membrane of a PCLMD chip. For example, first image 300 may be an image of membrane 106 of FIG. 1 (it is to be understood that first image 300 may be magnified relative to the schematic diagram shown in FIG. 1). The macro structure array 301 may include a plurality of pillar-like structures, such as double-cross pillar 302 which is shown in a magnified view in FIG. 3. The double-cross pillar 302 includes a first cross 304 (depicted in a dashed line outline in FIG. 3) and a second cross 306 (depicted in a solid line outline) super-imposed on the first cross 304. The second cross 306 may be angled relative to the first cross 304, e.g., positioned at an angle of 45° relative to the first cross. However, other macro structure shapes are possible, such as hexagon, union jack, etc. The double cross pillars described herein may be of similar size as the trophoblast cells and bind with the trophoblast cells with the eight arms of the pillars. The pillars may have a diameter of 10 µm, which provide strength to pillar structure and prevent the pillar structure from bending over during the fluid flow through the channels, so that the interaction between the pillars and cells is enhanced.

Each cross may be comprised of two arms of equal length, with one arm crossing the other arm at a center region of the cross. For example, first cross 304 may be comprised of an arm that extends vertically and an arm that extends horizontally, and the two arms may cross at a center of the first cross. Each cross may have a diameter d (shown in FIG. 3) that represents the length of one arm; when the two crosses are super-imposed to form the double-cross pillar, the double-cross pillar may have four arms of equal length, all having a length equal to the diameter d and all intersecting at the center of the double-cross pillar. In one example, the diameter d may be 10 µm, or other suitable length such as in a range of 8-12 µm. As appreciated by second image 310 of FIG. 3, the double-cross pillar macro structure array may selectively immobilize certain cells, such as a fetal trophoblast cell 312 shown in second image 310.

The macro structure array imprinted on the polymer membrane may include a plurality of pillar-like structures spaced apart from one another and distributed equally across the membrane surface. For example, double-cross pillar 302 may be spaced apart from a second double-cross pillar 308 by a suitable amount, such as 10-15 µm from a center of double-cross pillar 302 to a center of second double-cross pillar 308. The pillar-like structures may be distributed in the array in a suitable manner. As shown, the second double-cross pillar 308 is equally spaced from six other double-cross pillars (including the double-cross pillar 302) arranged around the second double-cross pillar 308 in a circular fashion, such that a center of the second double-cross pillar 308 is spaced approximately 10-15 µm from the center of each neighboring double-cross pillar. However, other array distributions and spacing are possible. By spacing the pillar-like structures in the above-described manner, cell capture of the target fetal cells may be enhanced.

Thus, a PCLMD chip for use in NIPT includes two features that may enhance isolation of fetal cells from a maternal blood sample, the functional microfluidic chip configuration and the double-cross pillar array for efficient cell enrichment. Two strategies for isolating rare cells in a sample include size selecting strategy and micro/nano structure assisted immobilization, which are combined together and realized by the microfluidic channel configuration and structure fabrication on an LMD chip, respectively. First, with the curved microfluidic channel, the cells with bigger size (more than 10 µm in diameter, such as trophoblast cells) are trapped selectively with longer retention time during sample flow through the channel, which gives greater chance to increase the contact time of the target fetal cells with the double-cross pillar array on the PCLMD chip. Secondly, the composite double-cross pillar structures having two orders of microstructure shows synergic function to immobilize the target cells. The macro structure of 10 µm as the diameter of a double-cross pillar blocks the target cell with similar size in the flow and the secondary microstructure enhances the interaction of the cell surface and the polystyrene substrate. Simultaneously, with the bio-affinity offered after the modification of surface with specific antibodies (described in more detail below), the adhesion of target cells on the substrate may be further enhanced.

Figure 4:
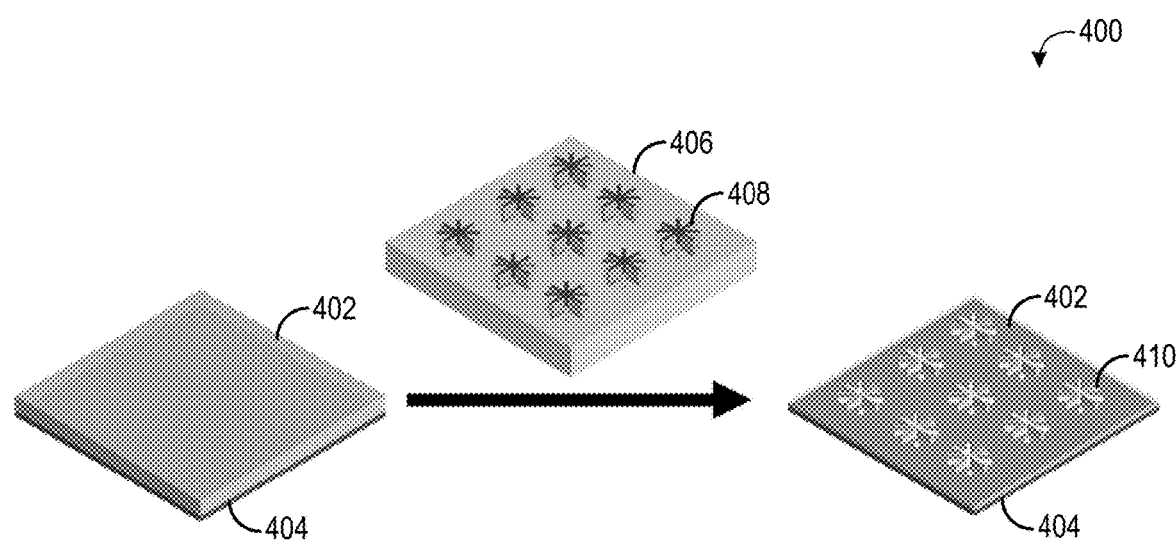
FIG. 4 illustrates an example process for imprinting a macro structure array on a polymer membrane of a PCLMD chip.

FIG. 4 schematically illustrates a process 400 for producing a macro structure array on a membrane of a PCLMD chip, such as PCLMD chip 100 of FIG. 1. As explained above, a polymer membrane 402, such as a polystyrene-amine membrane, is formed on a top surface of a substrate, such as glass slide 404. For example, the polymer membrane may be formed by spin coating a polymer solution (e.g., using a polystyrene-amine solution with 5% acetonitrile) on a glass slide or other suitable substrate at a suitable speed (e.g., 2000 RPM) to form a polymer membrane of a suitable thickness (e.g., 2-5 µm). A mold 406 is pressed on the polymer-coated slide. The mold 406 may be comprised of silicon or other material and include inverses of the pillar-like structures (e.g., double-cross pillar structure 408) formed via photolithography or other manufacturing technique. The mold 406 may be coated with hexamethyldisilazane (HMDS) and then pressed onto the polymer membrane 402 under pressure (e.g., 60 PSI) at high temperature (e.g., 130° C.) for a duration (such as 30 seconds). Once removed, the pillar-like structures, such as double-cross pillar 410, are formed on the membrane 402 at a suitable height, such as in a range of 0.2-2 µm (e.g., 0.5 µm). In some examples, the pillar-like structures may be formed only within the microfluidic channels of the substrate, and may not be present on other parts of the substrate. The mold 406 may be shaped to fit in the microfluidic channels.

Figure 5:
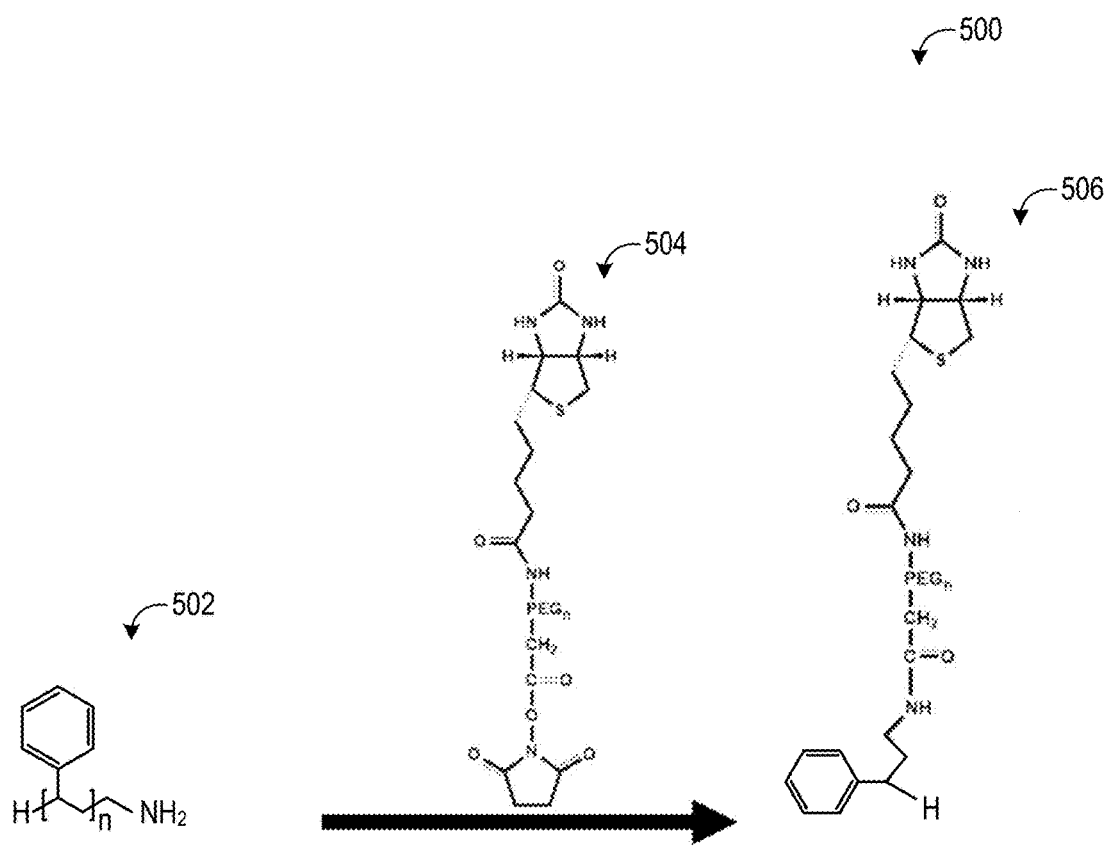
FIG. 5 illustrates an example process for adding biotin groups to a polymer membrane of a PCLMD chip.
Figure 6:
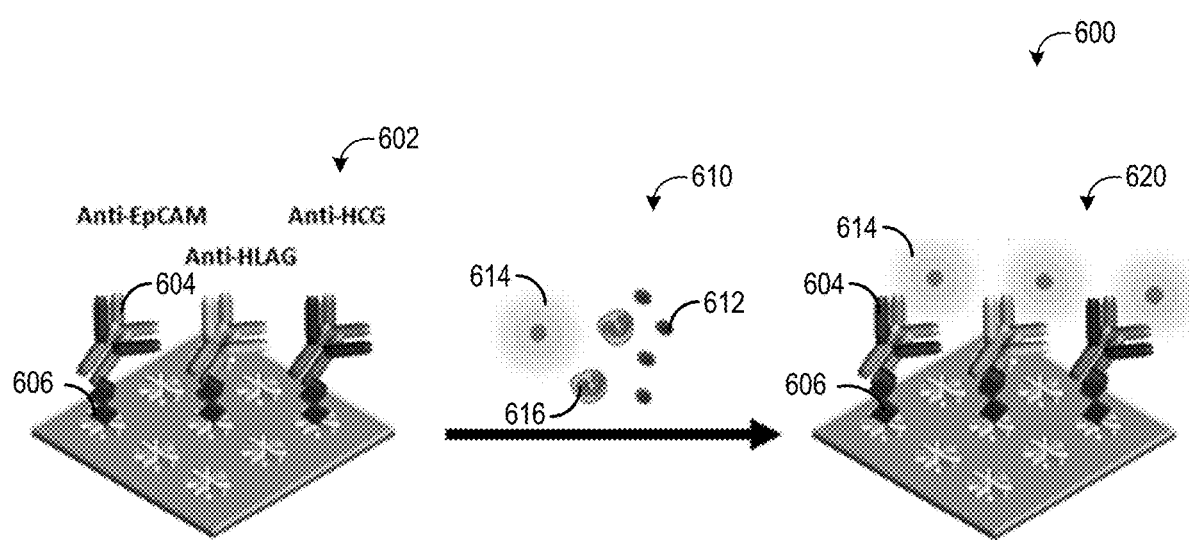
FIG. 6 illustrates an example process for isolating target cells with a functionalized PCLMD chip.

To make the PCLMD chip surface function with specific bio-affinity to enrich target cells, two procedures may be completed as illustrated in FIGS. 5 and 6. Firstly, as the surface of polystyrene membrane already has amine (—NH2) functional groups, a traditional method to introduce biotin using available molecules (e.g., NHS-PEG-Biotin) may be applied. As shown in the process 500 of FIG. 5, the polymer membrane may be comprised of polystyrene-amine 502. NHS-PEG-biotin 504 is applied to the membrane, causing biotin to be coupled to the amine group via the reactive N-hydroxysuccinimide ester (NETS), as shown at 506.

After the biotin functional group is modified on the PCLMD chip, through a generally used linker, neutravidin, antibodies may be coupled on the chip for trapping trophoblast cells. The three antibodies, anti-EpCAM, anti-HLAG, and anti-HCG, all have their corresponding antigens expressed specifically on trophoblast cells. As shown in the process 600 of in FIG. 6, antibodies are added to the polymer membrane at 602 using a neutravidin linker. For example, an antibody 604 (e.g., anti-EpCAM) may include a neutravidin linker 606 that binds to the biotin on the polymer membrane. In some examples, strepavidin or other linker may be used. Further, while anti-EpCAM, anti-HLAG, and anti-HCG antibodies are shown in FIG. 6, other antibodies may be used. The antibodies selected may be chosen based on the target cell type (e.g., antibodies may be selected that are specific to antigens expressed on the cell surface of the target cell type) and affinity for the antigens, for example.

As shown in FIG. 6, once the PCLMD chip is functionalized with antibodies, a sample may be passed over the PCLMD chip (e.g., via the microfluidic channels), as indicated at 610. The sample may be a maternal blood sample that includes red blood cells 612 (RBCs) and white blood cells 616 (WBCs) from the maternal blood supply, as well as a small proportion of fetal trophoblast cells 614. The trophoblast cells 614 may specifically bind to the antibodies present on the polymer membrane as shown at 620, in addition to being selectively immobilized via the long residence time in the microfluidic channels and the pillar-like structures on the polymer membrane.

Figure 7:
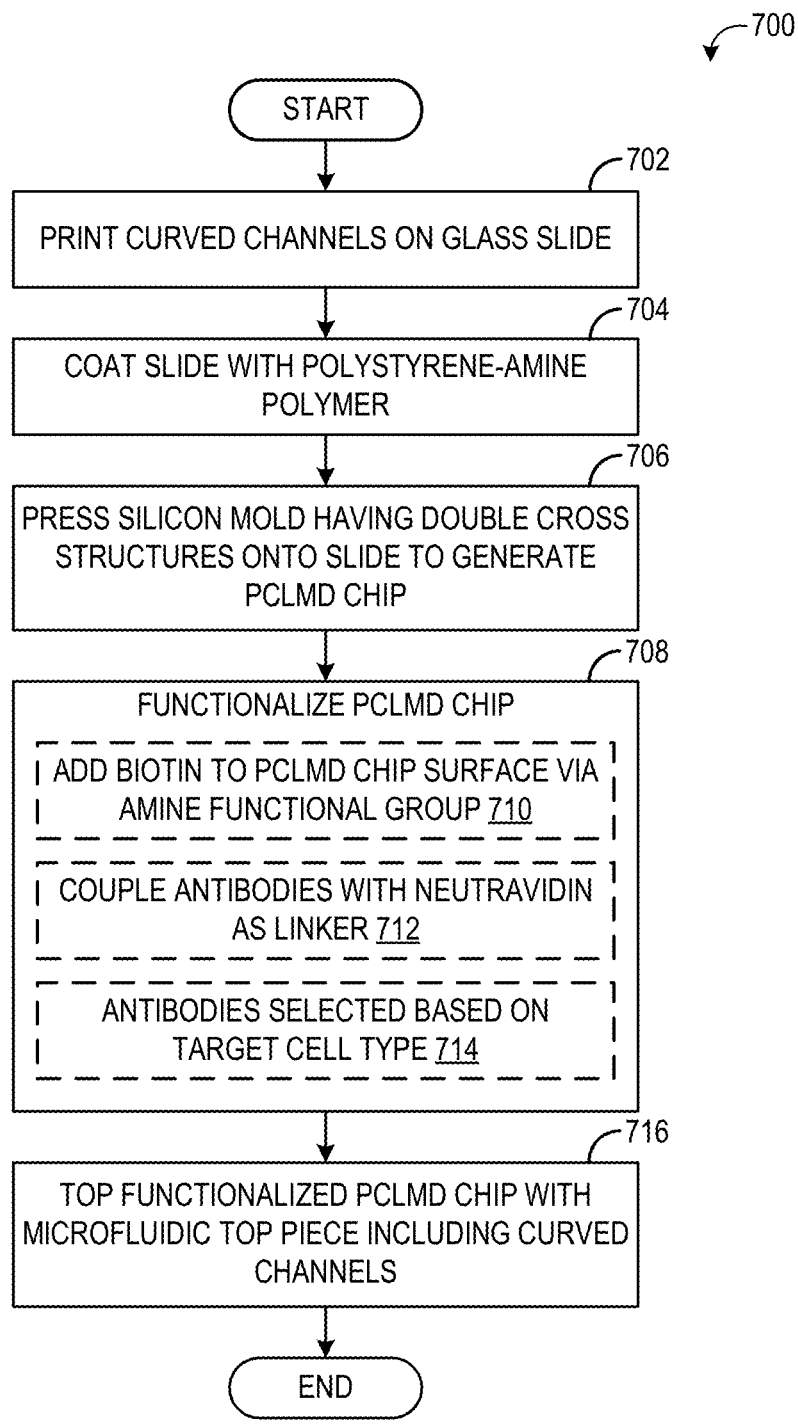
FIG. 7 is a flow chart illustrating an example method for manufacturing a PCLMD chip.

FIG. 7 is a flow chart illustrating a method 700 for manufacturing a PCLMD chip system for use in NIPT. For example, PCLMD chip system 200 of FIG. 2 may be manufactured according to the method 700 shown in FIG. 7. At 702, curved channels are printed on a substrate such as a pathology glass slide. The curved channels may include one or more microfluidic channels that each comprise a repeating pattern of two partial circles reversed relative to each other in order to form a switchback or serpentine shaped channel, such as the channels 104 shown in FIG. 1 and described above. The glass slide may be etched with the curved channels, and the glass slide may include a suitable number of channels, such as four channels, having a suitable number of curved portions, such as 11 top curved portions and 10 bottom curved portions.

At 704, the glass slide is coated with a polymer such as polystyrene-amine to form a polymer membrane having a thickness in a range of 2-5 µm. As described above with respect to FIG. 4, the polymer may be deposited using spin coating, with the polymer in a 5% acetonitrile solution and the spin coating being performed at 2000 RPM. At 706, a silicon mold having pillar-like structures, such as mold 406 of FIG. 4 including double-cross pillar structures, is pressed onto the polymer membrane, in order to form a polystyrene coated laser dissectible chip (PCLMD chip) having a macro structure array on the polystyrene membrane. As explained above with respect to FIG. 4, the silicon mold may be pressed under a pressure of 60 PSI at a temperature of 130° C. for a duration of 30 seconds, although other conditions are possible.

At 708, the PCLMD chip is functionalized. Functionalizing the PCLMD chip may include, as indicated at 710, adding biotin to the PCLMD chip surface via reaction with an amine functional group of the polystyrene membrane. For example, the polystyrene that is coated on the glass slide of the PCLMD chip may be polystyrene-amine, and thus the polystyrene membrane includes a functional group available to facilitate linkage to biotin. As explained above with respect to FIG. 5, biotin may be added to the polystyrene membrane via NHS-PEG-biotin, where the NHS is a reactive group that reacts with the amine to couple the biotin to the polystyrene. Functionalizing the PCLMD chip may further include, as indicated at 712, coupling antibodies to the biotin using neutravidin as a linker. For example, antibodies may be prepared with neutravidin or streptavidin as a linker and the antibodies may be supplied to the surface of the PCLMD chip, where the neutravidin or streptavidin may bind to the biotin. As indicated at 714, the antibodies may be selected based on the target cell type. For example, when the target cell type that is to be immobilized is a trophoblast, the antibodies that are selected may include anti-EpCAM, anti-HLAG, and/or anti-HCG.

At 716, the functionalized PCLMD chip is topped with a microfluidic top piece, such as the top piece 108 of FIG. 2, that may include curved channels that correspond to the curved channels printed on the PCLMD chip. The top piece also includes an inlet, an outlet, and suitable coupling mechanisms (e.g., inlet manifold and outlet manifold) to couple the inlet and outlet to the enclosed microfluidic channels that are formed with the top piece is coupled on the PCLMD chip. Method 700 then ends.

Thus, method 700 provides for the manufacture of a functionalized PCLMD chip that may be used to selectively isolate fetal cells circulating in a maternal blood supply. The functionalized PCLMD chip may include curved microfluidic channels though which a maternal blood sample may be flowed. The curved microfluidic channels may increase a retention time of the fetal cells relative to the maternal cells, due to the fetal cells being trophoblast cells, for example, which are relatively large compared to the maternal red and/or white blood cells. The functionalized PCLMD chip further includes a polystyrene membrane coating with structures imprinted on the polystyrene membrane that are configured to selectively trap the larger trophoblast cells. For example, the polystyrene membrane may be imprinted to form an array of pillar-like structures having a plurality of intersecting arms that are sized to trap the trophoblast cells (e.g., a diameter of 10 µm and height of 0.5 µm). The PCLMD chip may be functionalized to include biotin groups coupled to the polystyrene membrane via amine functional groups. The addition of the biotin allows for antibodies to be coupled to the polystyrene membrane prior to the maternal blood sample being supplied to the PCLMD chip. The antibodies may be specific to antigens present on the surface of the target cells, thereby further enhancing the isolation of the fetal cells from the maternal blood sample.

While method 700 was described above as including the addition of the antibodies prior to the topping of the PCLMD chip with the top piece, in some examples, the top piece may be added to the PCLMD chip before the antibodies are coupled to the biotin groups on the polystyrene membrane. For example, the antibodies may be present in a solution that is directed through the enclosed microfluidic channels before the maternal blood sample is flowed through the channels. In this way, a relatively complete and stable PCLMD chip may be produced, and the more sensitive antibodies may be added at the time of the sample testing.

Thus, FIG. 7 illustrates a method for manufacturing a polystyrene-coated laser micro-dissectible (PCLMD) chip usable for cell-based non-invasive prenatal testing. In one example, the method includes printing one or more curved microfluidic channels on a top surface of a glass slide, coating the top surface of the glass slide with a polystyrene membrane, imprinting a macro structure array on the polystyrene membrane, and placing a bottom surface of a top piece in face-sharing contact with the polystyrene membrane, the bottom surface including one or more corresponding curved microfluidic channels. In an example, the macro structure array may include a plurality of pillar-like structures each having a diameter of 10 μm, a height of 0.5 μm, and spaced apart from neighboring pillar-like structures by 15 μm. In an example, each pillar-like structure may be a double-cross structure comprised of two crosses that intersect at a center region of the double-cross structure, each cross comprised of two arms of equal length that intersect at the center region, and where one arm is angled at 45° relative to the other arm. Each arm may have a length of 10 μm.

Figure 8:
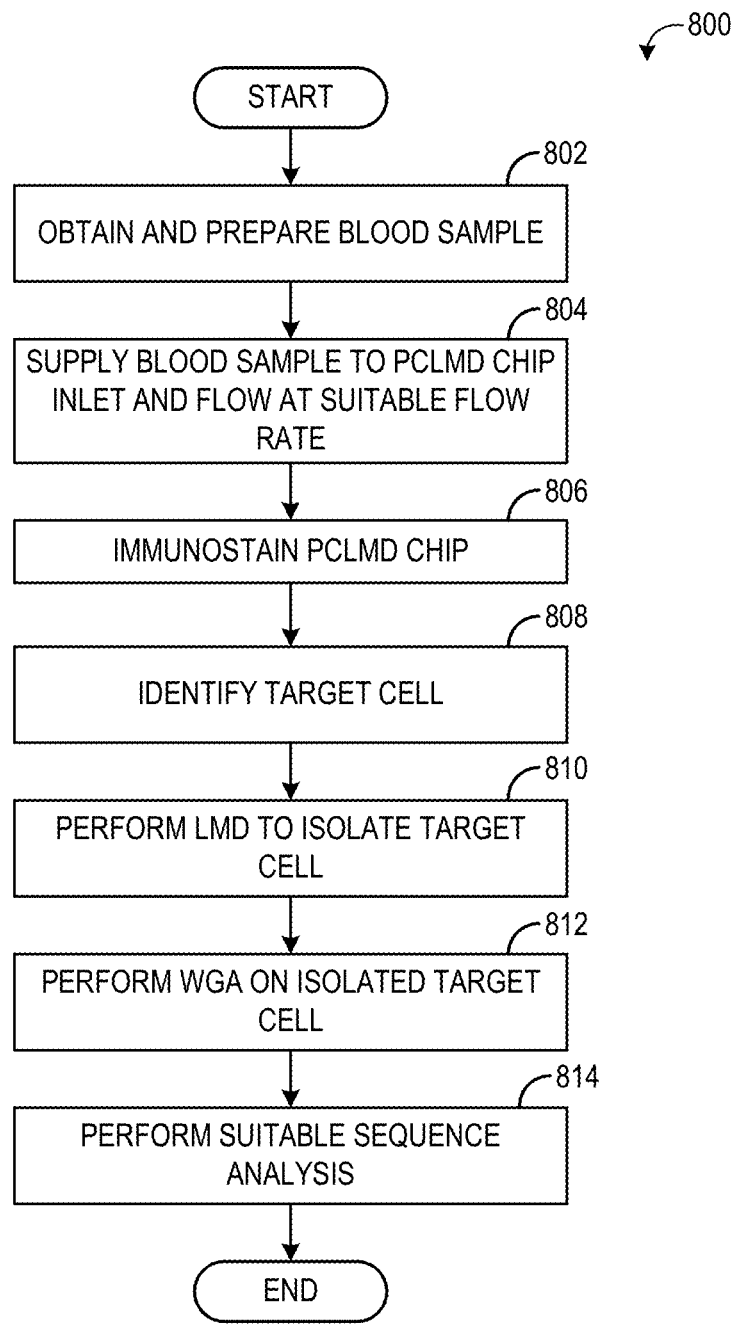
FIG. 8 is a flow chart illustrating an example method for performing cell-based non-invasive prenatal testing using a PCLMD chip.

FIG. 8 is a flow chart illustrating a method 800 for performing a cell-based non-invasive prenatal test using a PCLMD chip system, such as the PCLMD chip system described above with respect to FIGS. 1-7. At 802, a blood sample is obtained and prepared for testing. The blood sample may be a maternal blood sample obtained from a pregnant woman, for example. The blood sample may be prepared using standard PBMC isolation protocols, for example. At 804, the prepared blood sample is supplied to the inlet of the PCLMD chip system and is flowed through the enclosed microfluidic channels of the PCLMD chip system. The prepared sample may be flowed at a suitable flow rate, such as a rate between 0.1 and 2 mL/hour. The selected flow rate may balance efficiency (e.g., speed) and cell viability, and as the flow rate increases, cell viability decreases. In one example, the flow rate may be 0.5 mL/hour, which may provide a relatively high efficiency without compromising cell viability.

At 806, the PCLMD chip is immunostained with a selected set of markers that may help visualize the immobilized cells while differentiating the target fetal cells from maternal cells. For example, when the target fetal cells are trophoblasts, the PCLMD chip may be immunostained with DAPI and fluorophore-labeled antibodies against CK, HLAG, and CD45. Trophoblast cells may have a signature of DAPI+/CK+/HLAG+/CD45−, which may assist in differentiating the trophoblasts from maternal red blood cells (which will be DAPI−) and white blood cells (which will be CD45+). Immunostaining may be carried out according to standard immunostaining protocols.

At 808, a target fetal cell is identified. The target fetal cell may be identified by placing the immunostained PCLMD chip under a fluorescent microscope and exciting the fluorophores using the appropriate channels of the fluorescent microscope. As explained above, a target fetal cell may be identified based on the fluorescent signature of the cell matching an expected signature, such as the target trophoblast cell being identified based on the cell having a fluorescent signature of DAPI+/CK+/HLAG+/CD45−. Further, in some examples, the target cell may be additionally or alternatively identified based on cell size. For example, fetal trophoblast cells may have an average diameter of 16.5 μm, and cells that have a size of between 13 and 23 μm may be identified as trophoblast cells, in contrast to white blood cells, which may have an average diameter of approximately 6 μm. Further, while a cell may be identified as a fetal cell based on the mechanisms described above, the cell may be identified as a target fetal cell only if the cell is suitably isolated from other cells (e.g., maternal cells) so that the cell may be captured via laser microdissection, as described below. For example, an identified fetal cell may only be considered a target cell if the identified fetal cell is spaced away from any other cells by at least a threshold distance, such as 50 μm.

Figure 9:
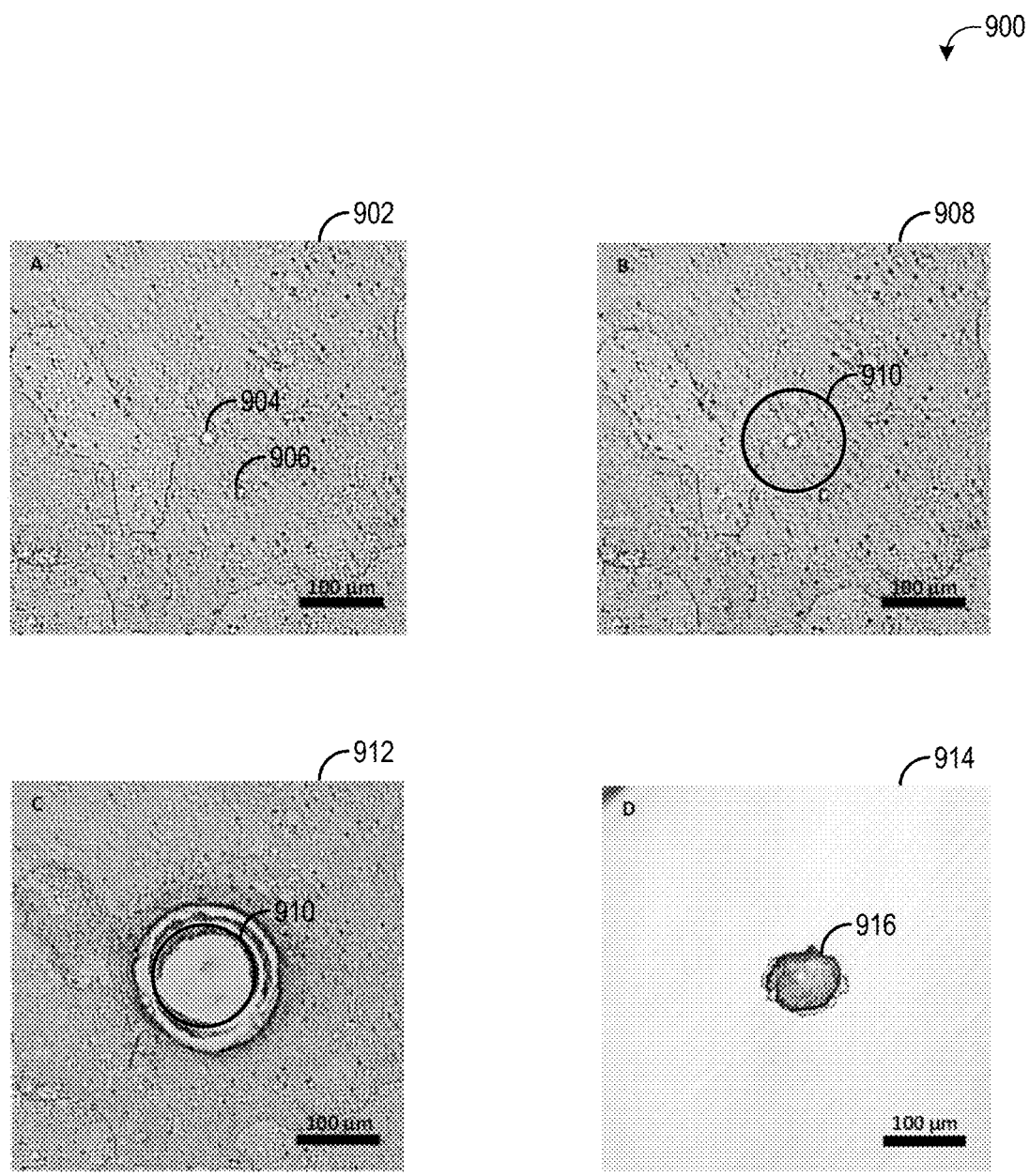
FIG. 9 is a series of images illustrating an example laser microdissection procedure.

Once a target cell is identified, laser microdissection is performed at 810 to isolate the target cell (if the top piece is not removed during the immunostaining or cell identification portions of the method, the top piece is removed prior to performing laser microdissection). FIG. 9 shows a series of images 900 that illustrate an example LIVID procedure. A first image 902 shows that two cells are immobilized on a PCLMD chip in the field of view. A first cell 904 is identified as a target fetal cell due to the size of the cell and/or immunostaining signature. A second cell 906 is identified as a non-target cell (e.g., the second cell may be a maternal cell). A second image 908 shows a user or system defined border 910 around the first cell. Laser microdissection is performed by focusing a laser beam on the border and moving the laser beam to follow the border. The laser beam width may be relatively narrow (e.g., 1 μm), leaving the target cell intact during laser microdissection. A third image 912 shows the PCLMD chip after the region within the border 910 has been cut out via the laser and removed. A fourth image 914 shows the region 916 that was cut out of the PCLMD chip, which includes the first cell. The entire region 916 (the polymer membrane and immobilized first cell) may be placed in a tube and subject to DNA amplification and analysis, as described below.

Returning to FIG. 8, at 812, whole genome amplification (WGA) is performed on the isolated target cell. WGA may be carried out using a suitable standard protocol, such as single cell comparative genomic hybridization or multiple displacement amplification.

At 814, suitable sequence analysis may be carried out on the amplified DNA from the target fetal cell. The sequence analysis may include standard prenatal genetic screening tests, such as analyses to determine aneuploidy and/or fetus sex. Further, in some examples, targeted sequence analysis may be performed to detect the presence of single gene disorders, genomic duplications, rearrangements, or other genetic abnormalities. Further, the sequence analysis may include analysis of short tandem repeats (STR) or other mechanism to confirm the DNA under analysis is from the target fetal cell and not from the maternal cells. For example, a plurality of STR alleles may be sequenced and compared to the sequences of the same STR alleles in a maternal DNA sample (e.g., prepared from maternal WBCs). Method 800 then ends.

Thus, the methods and systems described herein provide for a PCLMD chip system that includes a substrate, such as a glass slide, coated with a cell-capturing surface. The cell-capturing surface includes an array of pillar-like structures configured to selectively trap fetal cells. The cell-capturing surface may extend along a length, width, and height of microfluidic channel(s) present on the substrate. The pillar-like structure array and microfluidic asymmetric curved structure (repeating curved portions each shaped as three quarters of a circle) are configured for physically enriching trophoblast cells. To trap the trophoblast cells biologically, antibodies corresponding to specific antigens expressed on trophoblast cells were tested on artificial samples. For the artificial samples used in the following experiments, 500 choriocarcinoma cell line cells (such as BEWO, JEG3 and JAR) were spiked in 2 M white blood cells (WBCs) from blood of healthy donor in final 200 μL PBS solution. The spiking cell line cell was pre-stained with DIO and the WBCs were pre-stained with DID. Therefore, the resulting chip with immobilized cells on can be checked under fluorescence microscope (Nikon 90i) as convenience. As shown FIG. 10, the optimal condition for trophoblast cell enrichment is to use mixture of three antibodies with total concentration of 30 μM.

Figure 10:
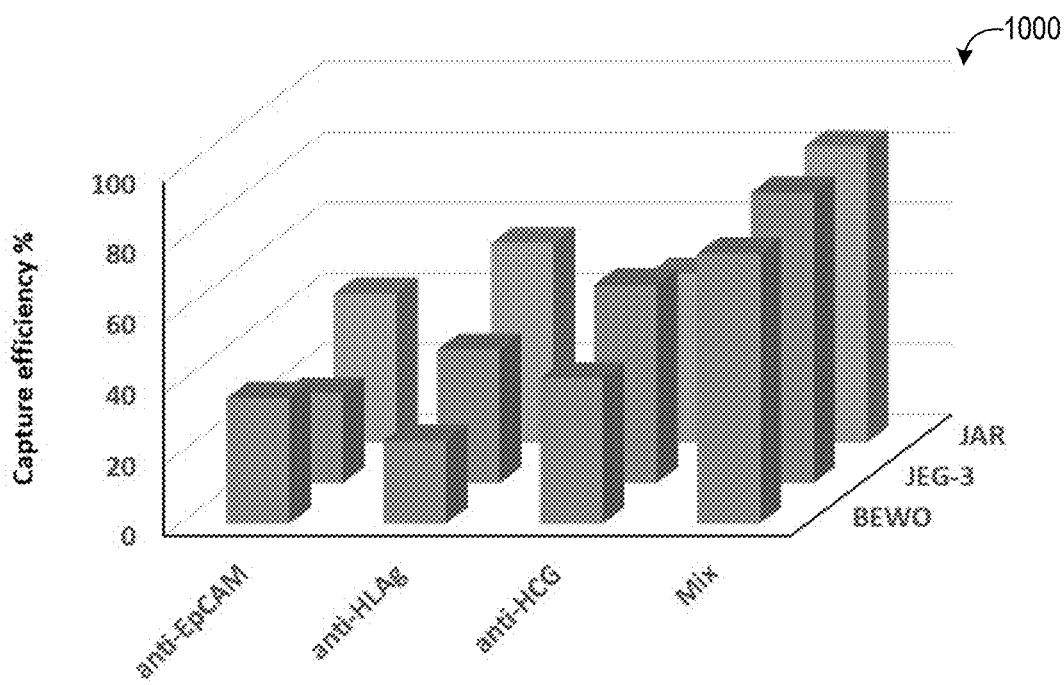
FIGS. 10-13 are graphs illustrating the effects of various PCLMD chip configurations on cell capture efficiency, viability, purity, and/or DNA quality.

FIG. 10 shows a graph 1000 demonstrating selection of specific antibodies for enrichment of trophoblast cells. Three choriocarcinoma cell lines were tested as artificial samples with different antibody or antibodies mixture modified microchip for the capture efficiency evaluation. As indicated, a mixture of antibodies shows overall highest enrichment efficiency as 76.5%, 82.3% and 83.9% for BEWO, JEG3 and JAR, respectively.

Figure 11:
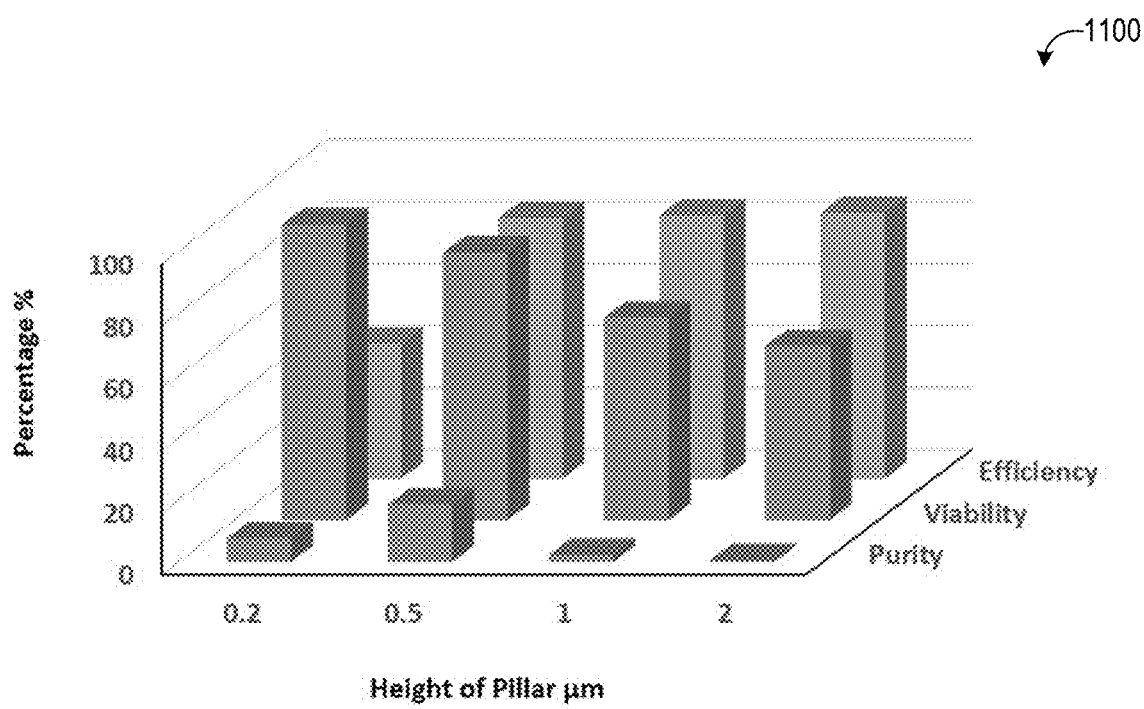

The height of the pillar-like structures in the array may give different physical interaction to trap and enrich trophoblast cells. In addition, the resulting physical interaction from different heights of pillars may affect the purity and viability of trapped cells. As shown in graph 1100 of FIG. 11, by testing the artificial samples based on JEG3, the pillar heights (0.2 μm, 0.5 μm, 1.0 μm and 2.0 μm) were evaluated on resulting trophoblast cell enriching efficiency, viability, and purity among non-specifically trapped WBCs. Considering the performance of trophoblast cell enrichment, arrays having pillar-like structures with height of 0.5 μm give the optimal purity of 18.5%, viability of 86.2%, and enrichment efficiency of 83.9%.

Figure 12:
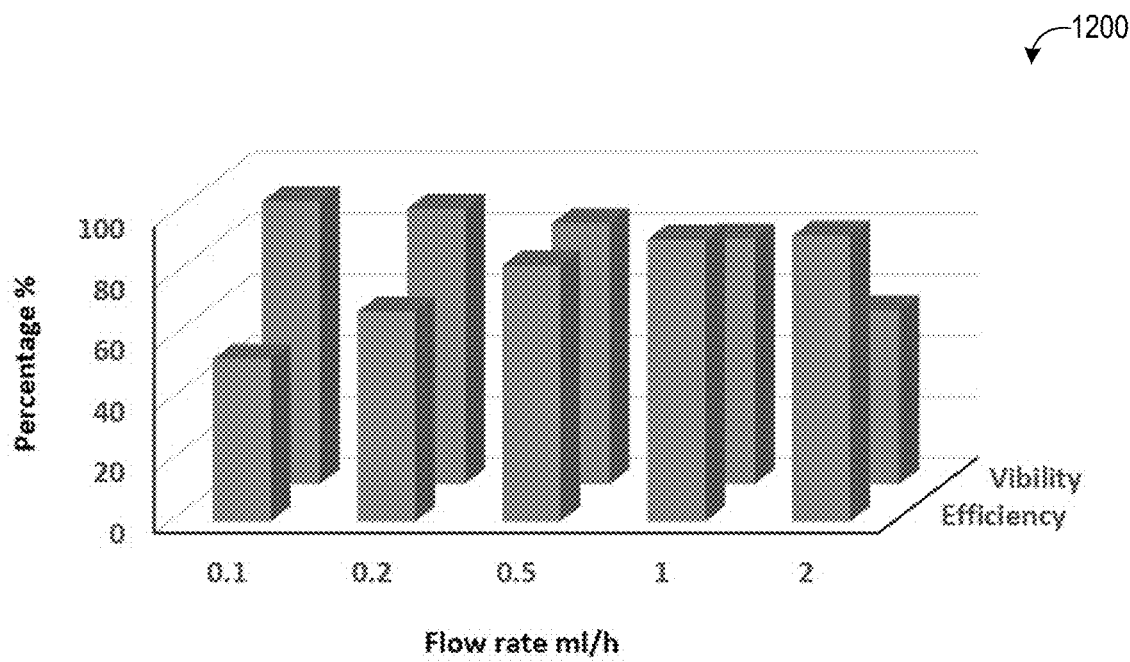

Five different flow rates in the asymmetric microfluidic channels for trophoblast cell enrichment were investigated by the performance on efficiency as well as viability. As indicated by graph 1200 of FIG. 12, the optimal condition is 0.5 mL/h with efficiency of 83.9 and viability of 85.3%.

Figure 13:
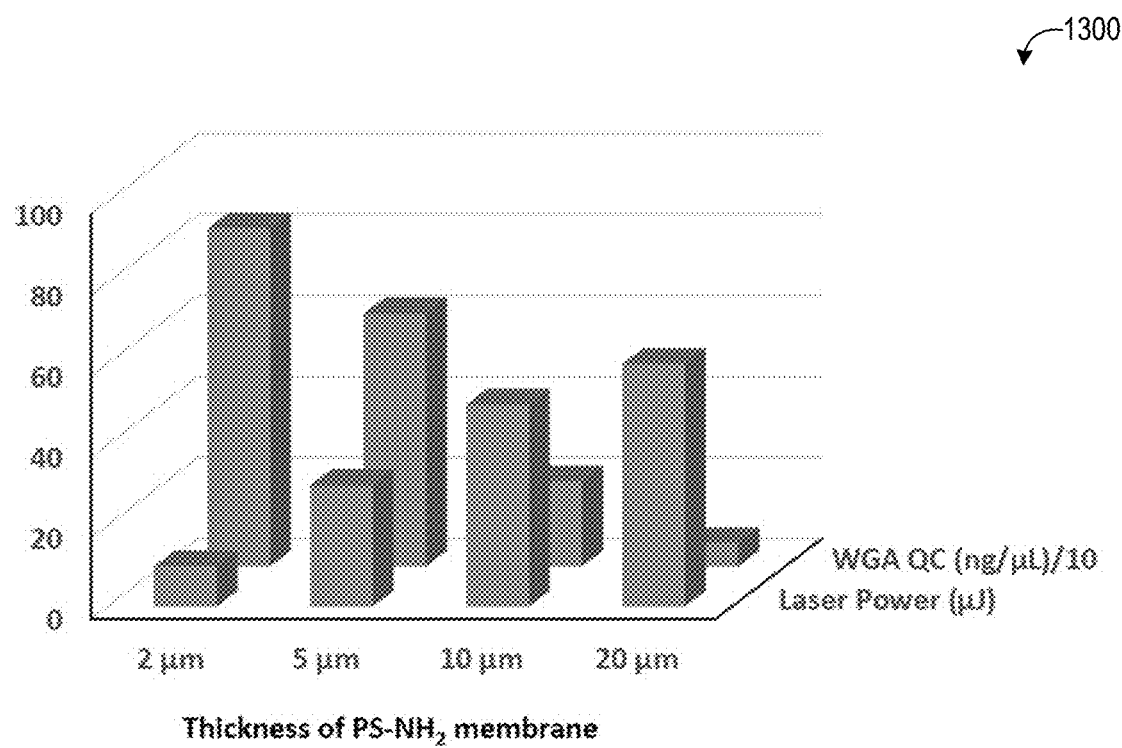

Once the trophoblast cells from the maternal blood are trapped on the PCLMD chip, cell imaging may be performed to identify the trophoblast cells and the identified cells may be captured using LIVID. With the increasing thickness of the polymer layer coating the PCLMD chip, the suitable laser power to cut through this polymer layer is increased. At the same time, the increasing laser power may trigger damage to cell DNA integrity and furtherly affect whole genome amplification results. By investigating WGA resulting DNA qualities (as shown by graph 1300 of FIG. 13), the optimal thickness of polymer layer may be 2.0 μm. While only thicknesses down to 2 μm are shown in FIG. 13, smaller thickness membranes are also possible, such as 1 μm.

Example 1

Fetal extravillous trophoblast cells (0001-EVTs) were isolated from a blood sample obtained from a pregnant woman using the PCLMD chip system described above with respect to FIGS. 1-7 and according to the method described above with respect to FIG. 8. WGA was performed on the isolated EVT cells to generate fetal genomic DNA suitable for further analysis. For comparison purposes, DNA samples were obtained from peripheral white blood cells (0001-WBCs) of the pregnant woman and from a product of concept (POC) (e.g., fetal tissue) upon spontaneous abortion occurring. Three EVTs were isolated, and the DNA harvested and amplified from the EVTs had a concentration of 850 ng/μL with quality scores of 0.3032 and 0.3093. Karyotyping of the DNA samples showed that the POC and EVTs each had 46 chromosomes with XY sex chromosomes while the WBCs had 46 chromosomes and XX sex chromosomes.

STR analysis was performed on the obtained DNA samples at 24 STR alleles. The STR fingerprints for the EVTs were the same as the POC and different than the WBCs, as shown in Table 1 below.

Next generation sequencing (NGS) results of 0001-EVTs show whole genomic information (including copy numbers of chromosomes of the whole genome). As well, the qualities of amplified DNA of 0001-EVTs are sufficiently high for NGS, STR, and other downstream genetic analysis. The conclusion shows target cells isolated using the PCLMD chip system disclosed herein can be used for downstream whole genome genetic analysis (including screening tests and/or diagnostic tests).

TABLE 1

| STR Alleles | POC | 0001-EVTs | 0001-WBCs |
| --- | --- | --- | --- |
| AMEL | X/Y | X/Y | X |
| D3S1358 | 14/17 | 14/17 | 15/17 |
| D1S1656 | 15 | 15 | 14/15 |
| D2S441 | 11/15 | 11/15 | 11 |
| D10S1248 | 14/15 | 14/15 | 15 |
| D13S317 | 8/12 | 8/12 | 8/12 |
| Penta E | 5/12 | 5/12 | 11/12 |
| D16S539 | 11/13 | 11/13 | 11 |
| D18S51 | 10/14 | 10/14 | 14 |
| D2S1338 | 17/20 | 17/20 | 17/20 |
| CSF1PO | 12 | 12 | 10/12 |
| Penta D | 10/13 | 10/13 | 11/13 |
| TH01 | 6/8 | 6/8 | 6/7 |
| vWA | 14/15 | 14/15 | 15/16 |
| D21S11 | 29/31.2 | 29/31.2 | 29 |
| D7S820 | 11 | 11 | 11/12 |
| D5S818 | 12 | 12 | 10/12 |
| TPOX | 8/11 | 8/11 | 10/11 |
| DYS391 | 10 | 10 | 8 |
| D8S1179 | 13 | 13 | 13 |
| D12S391 | 18/18.3 | 18/18.3 | 18/18.3 |
| D19S433 | 14/15 | 14/15 | 14/15 |
| FGA | 21/23 | 21/23 | 21/25 |
| D22S1045 | 15/16 | 15/16 | 11/16 |

Example 2

Fetal extravillous trophoblast cells (0002-EVTs) were isolated from a blood sample obtained from a pregnant woman using the PCLMD chip system described above with respect to FIGS. 1-7 and according to the method described above with respect to FIG. 8. WGA was performed on the isolated EVT cells to generate fetal genomic DNA suitable for further analysis. For comparison purposes, DNA samples were obtained from peripheral white blood cells (0002-WBCs) of the pregnant woman and from a product of concept (POC) (e.g., fetal tissue) upon spontaneous abortion occurring. Two EVTs were isolated, and the DNA harvested and amplified from the EVTs had a concentration of 786 ng/μL with quality scores of 0.2015 and 0.2051. Karyotyping of the DNA samples showed that the POC and EVTs each had 45 chromosomes with X0 sex chromosomes while the WBCs had 46 chromosomes and XX sex chromosomes.

STR analysis was performed on the obtained DNA samples at 24 STR alleles. The STR fingerprints for the EVTs were the same as the POC and different than the WBCs, as shown in Table 2 below.

NGS results of 0002-EVTs show whole genomic information (including copy numbers of chromosomes of the whole genome). As well, the qualities of amplified DNA of 0002-EVTs are sufficiently high for NGS, STR, and other downstream genetic analysis. The conclusion shows target cells isolated using the PCLMD chip system disclosed herein can be used for downstream whole genome genetic analysis (including screening tests and/or diagnostic tests).

TABLE 2

| STR Alleles | 0002-POC | 0002-EVTs | 0002-WBCs |
|---|---|---|---|
| AMEL | X | X | X |
| D3S1358 | 16 | 16 | 16 |
| D1S1656 | 17.3/18.3 | 17.3/18.3 | 17.3/18.3 |
| D2S441 | 11/13 | 11/13 | 11/13 |
| D10S1248 | 15 | 15 | 15 |
| D13S317 | 8/12 | 8/12 | 12 |
| Penta E | 10/17 | 10/17 | 10 |
| D16S539 | 11 | 11 | 11 |
| D18S51 | 14/17 | 14/17 | 14/17 |
| D2S1338 | 19/23 | 19/23 | 23/24 |
| CSF1PO | 10/12 | 10/12 | 10 |
| Penta D | 8/12 | 8/12 | 8/12 |
| TH01 | 6/7 | 6/7 | 6 |
| vWA | 16/17 | 16/17 | 16/17 |
| D21S11 | 30/33.2 | 30/33.2 | 30/33.2 |
| D7S820 | 10/12 | 10/12 | 10/12 |
| D5S818 | 11/12 | 11/12 | 11/12 |
| TPOX | 10/11 | 10/11 | 10/11 |
| DYS391 | 5/7/11 | 5/11 | 5/11 |
| D8S1179 | 10/17 | 10/17 | 10/17 |
| D12S391 | 16/19 | 16/19 | 16/18.3 |
| D19S433 | 15/15.2 | 15/15.2 | 15/15.2 |
| FGA | 23/24 | 23/24 | 23/24 |
| D22S1045 | 14/15 | 14/15 | 14/15 |

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed The subject matter of the present disclosure includes all novel and non-obvious combinations and sub-combinations of the various processes, systems and configurations, and other features, functions, acts, and/or properties disclosed herein, as well as any and all equivalents thereof.

What is claimed is:

1. A method for isolating fetal cells from a maternal blood sample, comprising: supplying, by a polymer-coated laser microdissectible (PCLMD) chip, the maternal blood sample to an inlet of a microfluidic channel of a laser micro-dissectible (LMD) chip; and flowing, by the PCLMD chip, the maternal blood sample through the microfluidic channel and over a polymer membrane coating one or more surfaces of the microfluidic channel, the polymer membrane comprising an array of structures, wherein the array of structures comprises an array of double-cross pillar structures, each double-cross pillar structure comprising two crosses intersecting at a center region of the double-cross pillar, each cross comprised of two arms of equal length intersecting at the center region, and wherein the double-cross pillar structures bind with the fetal cells to isolate fetal cells from a maternal blood sample.

2. The method of claim 1, wherein flowing the maternal blood sample through the microfluidic channel comprises flowing the maternal blood sample at a flow rate in a range of 0.1-2 mL/hour.

3. The method of claim 1, wherein flowing the maternal blood sample through the microfluidic channel comprises flowing the maternal blood sample through a plurality of curved portions of the microfluidic channel.

4. The method of claim 1, further comprising, before supplying the maternal blood sample to the inlet of the microfluidic channel, supplying one or more antibodies to the inlet of the microfluidic channel and flowing the one or more antibodies through the microfluidic channel, the one or more antibodies to bind to the polymer membrane using a neutravidin linker and raised against one or more antigens present on the fetal cells, and wherein the one or more antibodies comprises the neutravidin linker that binds to biotin on the polymer membrane.

5. The method of claim 1, further comprising capturing an identified fetal cell immobilized on the polymer membrane using laser microdissection.

6. A method for isolating fetal cells from a maternal blood sample using a system for non-invasive prenatal testing, comprising a substrate coated with a cell-capturing surface, the cell-capturing surface including an array of double-cross pillar structures, each double-cross pillar structure comprising two crosses intersecting at a center region of the double-cross pillar, each cross comprised of two arms of equal length intersecting at the center region, the method comprising the steps: supplying the maternal blood sample to an inlet of a microfluidic channel of a laser micro-dissectible (LIVID) chip; and flowing the maternal blood sample through the microfluidic channel and over a polymer membrane coating one or more surfaces of the microfluidic channel.

7. The method of claim 6, wherein the cell-capturing surface comprises a polystyrene membrane.

8. The method of claim 6, wherein the double-cross pillar structure including four arms that intersect at a center of the double-cross pillar structure, each arm having a length of 10 μm.

9. The method of claim 6, wherein the substrate includes a microfluidic channel and the cell-capturing surface extends along a length and width of the microfluidic channel.

\* \* \* \* \*